United States Patent [19]

Balzarini et al.

[11] Patent Number: 5,137,724
[45] Date of Patent: Aug. 11, 1992

[54] COMBINATIONS OF TS-INHIBITORS AND VIRAL TK-INHIBITORS IN ANTIHERPETIC MEDICINES

[75] Inventors: Jan M. R. Balzarini; Erik D. A. De Clercq, both of Heverlee, Belgium

[73] Assignee: Stichting Rega VZW, Belgium

[21] Appl. No.: 734,276

[22] Filed: Jul. 22, 1991

Related U.S. Application Data

[63] Continuation-in-part of Ser. No. 527,489, May 23, 1990, abandoned.

[51] Int. Cl.$^5$ .................. A61K 9/00; A61K 31/70; A01N 43/04
[52] U.S. Cl. .................. 424/400; 424/405; 424/430; 424/436; 424/451; 424/464; 424/489; 514/49; 514/50; 514/51; 514/934; 514/937
[58] Field of Search .............. 514/49, 50, 51, 934, 514/937; 424/405, 400, 451, 464, 436, 430, 489

[56] References Cited

U.S. PATENT DOCUMENTS

| | | | |
|---|---|---|---|
| 4,000,260 | 12/1976 | Prusoff et al. | 514/50 |
| 4,724,232 | 2/1988 | Rideout et al. | 424/451 X |
| 4,818,538 | 4/1989 | Rideout et al. | 424/451 X |
| 4,828,838 | 5/1989 | Rideout et al. | 424/451 |
| 4,833,130 | 5/1989 | Rideout et al. | 424/451 X |
| 4,837,208 | 6/1989 | Rideout et al. | 424/451 X |
| 4,847,244 | 7/1989 | Rideout et al. | 424/451 X |
| 4,882,316 | 11/1989 | Lambert et al. | 514/49 |
| 4,894,365 | 1/1990 | De Clerq et al. | 514/50 |
| 4,956,346 | 9/1990 | Lambert et al. | 514/50 |

FOREIGN PATENT DOCUMENTS 8300436 2/1983 World Int. Prop. O. ........... 514/51

*Primary Examiner*—Thurman K. Page
*Assistant Examiner*—Donald R. McPhail
*Attorney, Agent, or Firm*—Webb, Burden, Ziesenheim & Webb

[57] ABSTRACT

The antiviral activity of 5-fluoro-uracil, 5-fluoro-2'-deoxyuridine and similar thymilydate synthetase inhibitors towards herpes viruses can be potentiated dramatically by combining these compounds with compounds having viral thymidine kinase inhibiting activity.

8 Claims, No Drawings

COMBINATIONS OF TS-INHIBITORS AND VIRAL TK-INHIBITORS IN ANTIHERPETIC MEDICINES

This is a continuation-in-part of copending application Ser. No. 07/527,489 filed on May 23, 1990, and now abandoned.

This invention relates to a new medicine for use in the treatment of herpetic diseases, said medicine being based upon a combination of a group of viral thymidine kinase inhibitors which in themselves have no antiviral activity, with a group of thymidylate synthetase inhibitors which in themselves have only a moderate antiviral activity. The combination of both groups of compounds results into a potentiating effect on the antiviral activity of the thymidylate synthetase inhibitors.

Herpetic diseases are mild to severe diseases caused by certain viruses of the herpes family, such as e.g. herpes simplex type 1, herpes simplex type 2 and varicella zoster virus Although in most cases, these diseases have no lethal effect, they often show recurrent clinical episodes and may sometimes cause permanent damage to the skin or retina of a patient.

Several agents having strong antiviral activity towards herpes viruses have been found during the past 20 years. Among them can be mentioned: acyclovir or 9-(2-hydroxyethoxymethyl)-guanine, ganciclovir or 9-(1,3-dihydroxypropoxymethyl)-guanine, PMEA or 9-(2-phosphonylmethoxyethyl)-adenine and BVDU or (E)-5-(2-bromovinyl)-2'-deoxyuridine.

Each of these compounds may have its own field of utility based upon considerations of activity mechanism and selectivity. Nevertheless, there is a constant need for anti-herpes medicines of other nature which would have benefits in the treatment of herpetic diseases.

In accordance with the invention, it has now been found that a certain group of chemical compounds which are well known in anti-cancer therapy but which have only a moderate and non-selective antiviral activity toward herpes viruses, can be potentiated dramatically in their antiviral activities by combining them with a group of other compounds especially developed for research in the activity mechanism of herpes viruses.

Typical examples of the first-mentioned group of compounds are 5-fluoro-uracil and 5-fluoro-2'-deoxyuridine which have received wide application in cancer chemotherapy. Compare C. Heidelberger et al, Cancer Research, 23, 1226-1243 (1963). It is assumed that 5-fluoro-uracil is rapidly converted in vivo to 5-fluoro-2'-deoxyuridine and that the latter compound is really active in tumors The anti-cancer activity of these and related compounds is based upon the fact that they irreversibly inhibit thymidylate synthetase, a cell-growth promoting enzyme They can therefore be indicated as thymidylate synthetase inhibitors or TS inhibitors. They have only a moderate and non-selective antiviral activity towards herpes viruses.

Typical examples of the second-mentioned group of compounds are nucleoside analogues of formulae I and II:

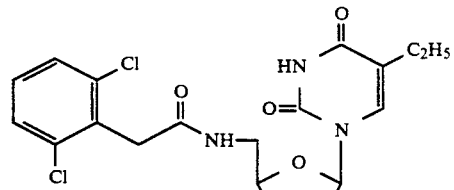

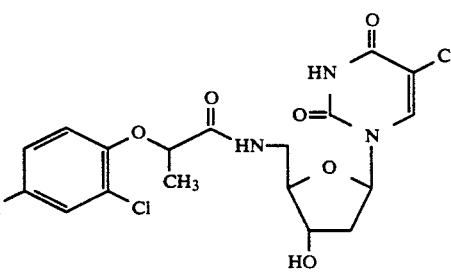

The compounds (I) and (II) as well as other 5'-substituted-5-ethyl-2',5'-dideoxyuridines appear to have an inhibitory effect on thymidine kinase, an enzyme present in herpes viruses without, however, showing any marked antiviral effect towards these viruses. Compare J. A. Martin et al, pages 103-115 in ACS Symposium Series No 401, Nucleotide Analogues as Anti-viral Agents, John C. Martin, Editor, 1989. They can be indicated as viral thymidine kinase inhibitors or viral TK-inhibitors.

As stated above, the TS-inhibitors 5-fluoro-uracil and 5-fluoro-2'-deoxyuridine have only a moderate and non-selective antiviral activity towards herpes viruses. Further, antiviral activity of the viral TK-inhibitors (I) and (II) can be regarded as negligible. Nevertheless, if 5-fluoro-2'-deoxyuridine is combined with either of compounds (I) and (II), it appears that its antiviral activity towards herpes viruses is potentiated dramatically, thus rendering such combination highly valuable as a medicine for use in the treatment of herpetic diseases.

Experiments have shown that compounds (I) and (II) also have a potentiating effect on the anti-viral activity of other compounds such as e.g. 5-fluoro-2'-deoxycytidine, 5-trifluoromethyl-2'-deoxyuridine and 5-ethynyl-2'-deoxyuridine. All these compounds are anti-cancer agents having a direct TS inhibiting activity, in the same way as 5-fluoro-2'-deoxyuridine. It may be assumed that the potentiating effect of compounds (I) and (II) is not restricted to the compounds as mentioned, however, and that it will also apply to precursors thereof such as e.g. 5-fluoro-uracil, 5-fluorocytosine, 5-trifluoromethyl-uracil and 5-ethynyl-uracil. Moreover, a potentiating effect of compounds (I) and (II) will also be present in combinations with active compounds (such as e.g. methotrexate or MTX) which have an indirect TS-inhibiting activity through inhibition of dihydrofolate reductase. In general, therefore, all compounds having direct or indirect thymidylate synthetase inhibiting activity will be susceptible to a potentiating effect of compounds (I) and (II). Such TS-inhibiting compounds or TS-inhibitors are useful as an antiherpes ingredient in the combinations of the present invention.

On the other hand, while the potentiating effect of compounds (I) and (II) on the antiviral activity of TS-inhibitors has experimentally been confirmed, it may be assumed that a similar potentiating effect is shown by other 5-ethyl-5'-substituted-2',5'-dideoxyuridines and in general by all nucleoside analogues and precursors that have a herpes viral TK-inhibiting activity. Such compounds termed viral TK-inhibitors are therefore useful as a potentiating ingredient in the combinations of the invention.

The potentiating effect of viral TK-inhibitors on the antiviral effect towards herpes viruses of TS-inhibitors is illustrated by the following experiment. Some well-known anti-herpes agents (ASV, DHPG and PMEA) were used for comparison therein.

In this experiment, the potentiating compounds $C_1$ and $C_2$ corresponded to formula I and formula II respectively. They were a gift from Dr. J. A. Martin of Roche Products Limited, Welwyn Garden City, England. Further, the following anti-herpes compounds were used:
ACV: 9-(2-hydroxyethoxymethyl)-guanine,
DHPG: 9-(1,3-dihydroxypropoxymethyl)-guanine,
PMEA: 9-(2-phosphonylmethoxyethyl)-adenine
FdUrd: 5-fluoro-2'-deoxyuridine
FdCyd: 5-fluoro-2'-deoxycytidine
$CF_3$dUrd: 5-trifluoromethyl-2'-deoxyuridine
Ethynyl-dUrd: 5-ethynyl-2'-deoxyuridine.
Most of these compounds were obtained through commercial channels, except PMEA which was a gift from Dr. Holy, Prague.

EXPERIMENT

The potentiating effect of compounds $C_1$ and $C_2$ on the anti-viral activity of several anti-herpes compounds was tested on herpes simplex virus type 2 (HSV-2) in primary rabbit kidney cells (PRK-cells).

Confluent monolayers of PRK-cells cultured in Eagle's minimum essential medium (EMEM) in the wells of a microtiter (R) tray were inoculated with 100 $CCID_{50}$ of HSV-2 test virus (1 $CCID_{50}$ represents the amount of virus required for infection of 50% of the cells under the prevailing conditions).

Then, the virus solution was removed and the cells were washed with EMEM and cultivated in solutions of EMEM containing various concentrations (wt/vol) of the anti-herpes test compounds together or not together with 40 $\mu$M of compound $C_1$ or 20 $\mu$M of compound $C_2$. (1M is one millimole per millileter). The cytopathogenic effect (CPE) of the virus in these cell cultures was evaluated at a time when the same virus had reached a CPE of 100% in a control culture, i.e. a culture wherein the cells were cultivated in EMEM without any test compound. The anti-viral effect was obtained from a series of measurements at various concentrations of the anti-herpes test compounds and was expressed as 50% effective concentration ($\mu$g/ml), i.e. the concentration of the test compound (with or without $C_1$ or $C_2$) which reduces the CPE of the virus to 50%. The resulting values are represented in the following table.

TABLE

| Compound | 50% effective concentration ($\mu$g/ml) |
| --- | --- |
| ACV | 0.11 |
| + $C_1$ (40 $\mu$M) | 19.6 |
| + $C_2$ (20 $\mu$M) | 17.5 |
| DHPG | 0.34 |
| + $C_1$ | 9.5 |
| + $C_2$ | 20 |
| PMEA | 8 |

TABLE-continued

| Compound | 50% effective concentration ($\mu$g/ml) |
| --- | --- |
| + $C_1$ | 7 |
| + $C_2$ | 7 |
| FdUrd | 33 |
| + $C_1$ | 0.032 |
| + $C_2$ | 0.034 |
| FdCyd | 2.62 |
| + $C_1$ | 0.01 |
| + $C_2$ | 0.03 |
| $CF_3$dUrd | 4.67 |
| + $C_1$ | 0.21 |
| + $C_2$ | 0.23 |
| Ethynyl-dUrd | 20 |
| + $C_1$ | 0.5 |
| + $C_2$ | 0.6 |

The following conclusions can be derived from the table: ACV (acyclovir) and DHPG (ganciclovir) are anti-herpes compounds which have a strong anti-viral activity in themselves. They are less active in the presence of a viral TK inhibitor (compound $C_1$ or $C_2$) which means that their activity depends on thymidine kinase of the virus.

PMRS is a moderate anti-herpes compound in itself Its activity is not influenced by the presence of compounds $C_1$ and $C_2$, which means that it does not need viral thymidine kinase to become antivirally active.

On the other hand, it appears from the table that FdUrd, FdCyd, $CF_3$dUrd and Ethynyl-dUrd are moderately active anti-herpes compounds and that their antiviral activity can be potentiated dramatically by the presence of compounds $C_1$ and $C_2$. In other words: these TS-inhibitors need a viral TK-inhibitor in order to display their maximum possible anti-viral activity.

The medicine of the present invention may be a single pharmaceutical composition which comprises a combination of a TS-inhibitor (as an anti-herpes ingredient) with a viral TK-inhibitor (as a potentiating ingredient), but it may also comprise two separate compositions which are to be administered in combination, viz. a composition containing a TS-inhibitor and a composition containing a viral TK-inhibitor.

The composition may have the form of suspensions, solutions, emulsions, ointments, creams, syrups, granulates, powders, tablets, dragees, capsules, pills, ampoules or suppositories and may be used for topical, intranasal, ocular, rectal or vaginal application or else for oral or parenteral (intravenous, intradermal, intramuscular, intrathecal etc.) administration.

Such compositions may be prepared by combining (e.g. mixing, dissolving, kneading, compressing, encapsulating etc) the anti-herpes ingredient and/or the potentiating ingredient with pharmaceutically acceptable excipients of inert nature, such as aqueous or non-aqueous solvents together with stabilisers, emulsifiers, detergents, additives and the like. Suitable excipients for suspensions are e.g. water, ethanol, propylene glycol, surface-active agents (e.g. polyoxyethylene esters), micro crystalline cellulose, bentonite, agar-agar, tragacanth or mixtures thereof. Suitable excipients for solutions and emulsions are e.g. water, ethanol, isopropanol, ethyl carbonate, ethyl acetate, benzyl alcohol, benzyl benzoate, propylene glycol, dimethylformamide, oils (for example ground nut oil), glycerol, polyethylene glycols and fatty acid esters of sorbitol or mixtures thereof. Suitable excipients for ointments and creams are e.g. water, glycerol, propylene glycol, cetyl alcohol, stearic acid, triethanol amine and liquid waxes.

A special form of solutions are those which can be used for ocular administration, e.g. as eyedrops. Such solutions should have a slightly acidic pH and may contain water as an excipient together with boric acid and other additives such as e.g. borax, phenylmercuric borate and benzalconium chloride.

Suitable excipients for granulates, tablets, dragees, capsules and pills will include: fillers and extenders, e.g. starch, sugars, mannitol; binding agents, e.g. carboxymethyl cellulose, alginates, gelatine; moisturizing agents, e.g. glycerol; disintegrating agents, e.g. agar, calcium carbonate and sodium bicarbonate; agents for retarding dissolution, e.g. paraffin; resorption accelerators, e.g. quaternary ammonium compounds; surface active agents, e.g. cetyl alcohol, glycerol monostearate; adsorptive carriers, e.g. kaoline and bentonite; and lubricants, e.g. talc, calcium and magnesium stearate and solid polyethyleneglycols. The tablets, dragees, capsules and pills may have the customary coatings, envelopes and protective matrices, made for example from polymeric substances or waxes.

The excipients for suppositories may be e.g. polyethylene glycols and fats or mixtures thereof.

The pharmaceutical compositions can also contain coloring agents, preservatives, perfumes, flavoring additions and sweetening agents.

The concentration of the active ingredient in any composition may vary between 0.1% and 99.9%, dependent from the route of administration.

The following formulations are representative for the pharmaceutical compositions of the invention.

A simple intravenous injection composition can be formed by dissolving 1 g of active ingredients (antiherpes ingredient and/or potentiating ingredient) into 250 ml of injectable saline. After filtering, the solution is packaged in sterile bottles.

A solution for intramuscular or intraperitoneal injection can be based on the following formulation:

| active ingredients | 0.2-5 g |
| --- | --- |
| polyethylene glycol | 50 g |
| propylene glycol | 50 g |
| span emulsifier | 2 g |
| injectable saline | 200 ml |

The first four materials are combined whereupon the injectable saline is added. The material forms a clear solution which is filtered and sealed in sterile bottles.

An ointment for topical administration may have the following base formulation:

| cetyl alcohol | 15 g |
| --- | --- |
| white wax | 1 g |
| propylene glycol | 10 g |
| sodium lauryl sulphate | 2 g |
| water | 72 g |

The active ingredients (5 g) are combined with the non-aqueous materials by stirring at 50° C. Then, water is stirred into the mixture at 50° C. to form an ointment and the mixture is cooled and packaged in tubes.

For eyedrops, the following formulations may be used:

| active ingredients | 1-25 g |
| --- | --- |
| boric acid | 16.5 g |
| benzalkonium chloride | 0.1 g |
| injectable saline | up to 1000 ml |
| or | |
| active ingredients | 1-25 g |
| boric acid | 15.5 g |
| borax | 0.5 g |
| phenylmercuric borate | 0.005 g |
| injectable saline | up to 1000 ml |

The latter two compositions are prepared by dissolving the non-aqueous ingredients into a small amount of saline by stirring and then adding the remaining amount of saline. The resulting compositions have a pH of 4.8 and 6.5 respectively and are packaged in sterile bottles.

What we claim is:

1. A medicine for use in the treatment of herpetic diseases, said medicine comprising an active antiherpes ingredient selected from the group consisting of 5-fluoro-2'-deoxyuridine, 5-fluoro-2'-deoxycytidine, 5-trifluoromethyl-2'-deoxyuridine and 5-ethynyl-2'-deoxyuridine, in combination with a potentiating ingredient selected from the group consisting of a compound of formula I or formula II:

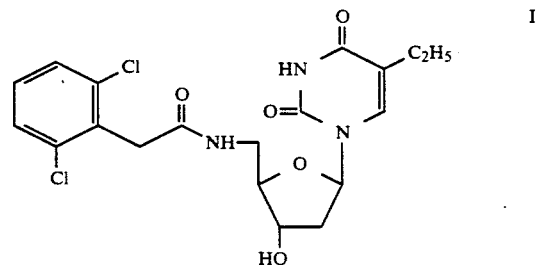

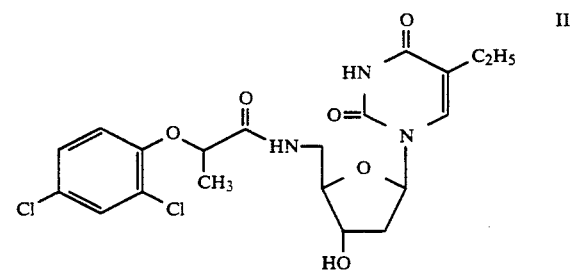

, wherein the ratio between said active anti-active herpes ingredient and said potentiating ingredient is between 1:10 and 100:1.

2. The medicine as claimed in claim 1, wherein said antiherpes ingredient is 5-fluoro-2'-deoxyuridine.

3. The medicine as claimed in claim 1, which has the form of a single composition.

4. The medicine as claimed in claim 1, which has the form of 2 separate compositions.

5. A method for the treatment of herpetic diseases, which comprises administering an active antiherpes ingredient selected from the group consisting of 5-fluoro-2'-deoxyuridine, 5-fluoro-2'-deoxycytidine, 5-trifluoromethyl-2'-deoxyuridine and 5-ethynyl-2'-deoxyuridine, in combination with a potentiating ingredient selected from the group consisting of a compound of formula I or formula II:

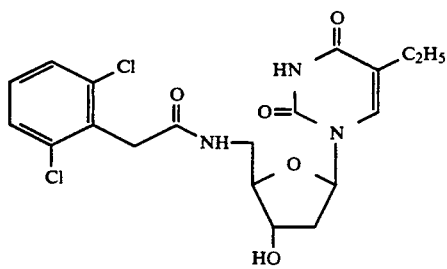

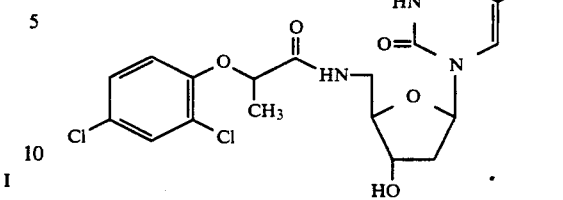

, wherein the ratio between said active antiherpes ingredient and said potentiating agent is between 1:10 and 100:1, to a patient in need of said treatment.

6. The method as claimed in claim 5, wherein said active anti-herpes ingredient is 5-fluoro-2′-deoxyuridine.

7. The method as claimed in claim 5, wherein said ingredients are administered in the form of a single composition.

8. The method as claimed in claim 5, wherein said ingredients are administered in the form of two separate compositions.

* * * * *